United States Patent [19]

Ferrari et al.

[11] 4,362,721
[45] Dec. 7, 1982

[54] PENICILLANIC AND CEPHALOSPORANIC DERIVATIVES, PREPARATION THEREOF, AND PHARMACEUTICAL COMPOSITIONS CONTAINING SAME

[75] Inventors: Giorgio Ferrari; Vittorio Vecchietti, both of Milan, Italy

[73] Assignee: Simes S.p.A., Italy

[21] Appl. No.: 327,058

[22] Filed: Dec. 3, 1981

Related U.S. Application Data

[63] Continuation-in-part of Ser. No. 205,332, Nov. 10, 1980, abandoned.

[30] Foreign Application Priority Data

Nov. 9, 1979 [IT] Italy .............................. 27147 A/79

[51] Int. Cl.³ .......................... A61K 31/70; C07H 15/26
[52] U.S. Cl. ..................................... 424/180; 536/53; 536/17.3
[58] Field of Search .................. 536/4, 22, 18, 53; 544/27, 28; 424/180

[56] References Cited

U.S. PATENT DOCUMENTS

| | | | |
|---|---|---|---|
| 4,025,622 | 5/1977 | Ogura et al. | 536/22 |
| 4,041,161 | 9/1977 | Kocsis et al. | 544/27 |
| 4,285,940 | 9/1981 | Machida et al. | 544/28 |
| 4,285,941 | 9/1981 | Machida et al. | 544/27 |

FOREIGN PATENT DOCUMENTS

28803 6/1981 European Pat. Off. .

*Primary Examiner*—Blondel Hazel
*Attorney, Agent, or Firm*—Stevens, Davis, Miller & Mosher

[57] ABSTRACT

There are disclosed penicillanic and cephalosporanic derivatives of the formula:

(I)

wherein R is H or —OH; $R_1$ is a carbohydrate hexose radical of 3-O-glucose, 6-O-galactose, 3-O-glucose acetals, 3-O-glucose ketals, 6-O-galactose acetals, and 6-O-galactose ketals, and $R_2$ is:

where $R_3$ is H or an alkali or alkaline-earth metal. The preparation of the derivatives and pharmaceutical compositions containing same are also disclosed.

A process according to the invention comprises reacting a compound of the formula with a hexose carbohydrate, in —OH protected form, in an aqueous medium, in the presence of a water-miscible organic solvent, in the presence of a base, the reaction product being optionally transformed into the derivative wherein $R_1$ is a carbohydrate in the unprotected form by treatment with Lewis' acid or a hydrogen halide acid.

The compounds according to the invention are used in pharmaceutical compositions useful for treatment of infections by gram-positive and gram-negative pathogenous bacteria.

29 Claims, No Drawings

PENICILLANIC AND CEPHALOSPORANIC DERIVATIVES, PREPARATION THEREOF, AND PHARMACEUTICAL COMPOSITIONS CONTAINING SAME

REFERENCE TO RELATED APPLICATIONS

This is a continuation-in-part of the copending application Ser. No. 205,332 filed Nov. 10, 1980 now abandoned.

The present invention relates to new penicillanic and cephalosporanic derivatives, more particularly to optically active forms (D-isomers) of these compounds and to the preparation and use thereof.

The compounds according to the invention have the formula:

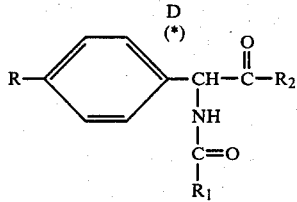

wherein R is H or —OH; $R_1$ is a hexose carbohydrate radical selected from the group consisting of 3-O-glucose, 6-O-galactose, 3-O-glucose acetals, 3-O-glucose ketals, 6-O-galactose acetals, and 6-O-galactose ketals, $R_2$ is a member selected from the group comprising:

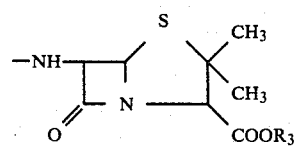

and

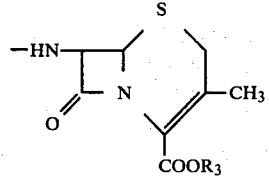

wherein $R_3$ is H or an alkali or earth-alkaline metal. The hexose derivatives are prepared by reacting them with a suitable reagent such as benzaldehyde, acetone, and cyclohexanone.

Both the cyclic and the linear form of the hexoses are encompassed within the scope of this invention.

When the hexose is in cyclic form, the radical $R_1$ may be represented by the following formulae:

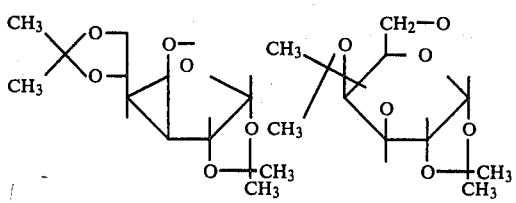
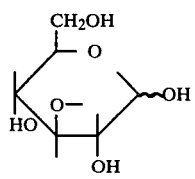
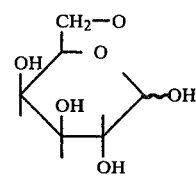
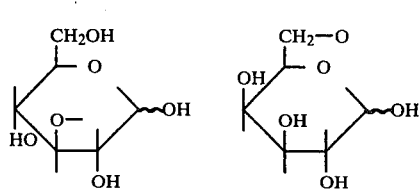

The following compounds fall within the present invention:

(1) 6-[D(—)-α-(1,2,3,4-diisopropylidene-D-galactopyranoside-6-O-carboxamido)-phenylacetamido]-3,3-dimethyl-7-oxo-4-thia-1-azabicyclo-[3,2,0]-heptane-2-carboxylic acid.

(2) 7-[D(—)-α-(1,2,3,4-diisopropylidene-D-galactopyranoside-6-O-carboxamido)-phenylacetamido]-3-methyl-8-oxo-5-thia-1-azabicyclo-[4,2,0]-oct-2-ene-2-carboxylic acid.

(3) 6-[D(—)-α-(1,2,5,6-diisopropylidene-D-glucofuranoside-3-O-carboxamido)-phenylacetamido]-3,3-dimethyl-7-oxo-4-thia-1-azabicyclo-[3,2,0]-heptane-2-carboxylic acid.

(4) 7-[D(—)-α-(1,2-5,6-diisopropylidene-D-glucofuranoside-3-O-carboxamido)-phenylacetamido]-3-methyl-8-oxo-5-thia-1-azabicyclo-[4,2,0]-oct-2-ene-2-carboxylic acid.

(5) 7-[D(—)-α-(D-galactose-6-O-carboxamido)-phenylacetamido]-3-methyl-8-oxo-5-thia-1-azabicyclo-[4,2,0]-oct-2-ene-2-carboxylic acid.

(6) 6-[D(—)-α-(D-galactose-6-O-carboxamido)-phenylacetamido]-3,3-dimethyl-7-oxo-4-thia-1-azabicyclo-[3,2,0]-heptane-2-carboxylic acid.

(7) 7-[D(—)-α-(D-glucose-3-O-carboxamido)-phenylacetamido]-3-methyl-1-oxo-5-thia-1-azabicyclo-[4,2,0]-oct-2-ene-2-carboxylic acid.

(8) 6-[D(—)-α-(D-glucose-3-O-carboxamido)-phenylacetamido]-3,3-dimethyl-7-oxo-4-thia-1-azabicyclo-[3,2,0]-heptane-2-carboxylic acid.

(9) 6-[D(—)-α-(1,2-3,4-diisopropylidene-D-galactopyranoside-6-O-carboxamido)-p-hydroxyphenylacetamido]-3,3-dimethyl-7-thia-1-azabicyclo-[3,2,0]-heptane-2-carboxylic acid.

(10) 6-[D(—)-α-(1,2-5,6-diisopropylidene-D-glucofuranoside-3-O-carboxamido)-p-hydroxyphenylacetamido]-3,3-dimethyl-7-oxo-4-thia-1-azabicyclo-[3,2,0]-heptane-2-carboxylic acid.

(11) 6-[D(—)-α-(D-galactose-6-O-carboxamido)-p-hydroxyphenylacetamido]-3,3-dimethyl-7-oxo-4-thia-1-azabicyclo-[3,2,0]-heptane-2-carboxylic acid.

(12) 6-[D(—)-α-(D-glucose-3-O-carboxamido)-p-hydroxyphenylacetamido]-3,3-dimethyl-7-oxo-4-thia-1-azabicyclo-[3,2,0]-heptane-2-carboxylic acid.

It has been found that the compounds of formula (I), when $R_1$ is the radical A or B, can be prepared by reacting a compound of the formula (II):

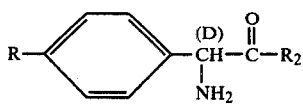

(wherein R and R₂ have the previously specified meanings and R₃ is H, an alkali or earth-alkaline ion) with a compound of the formula (IIIA) or (IIIB) according to whether R₁ is A or B:

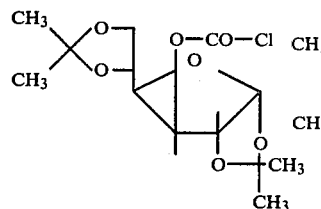 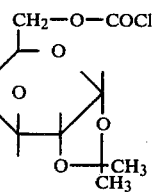

(IIIA)                                    (IIIB)

The reaction is carried out in an aqueous medium in the presence of water-miscible organic solvents such as acetone, tetrahydrofuran, dioxane, and diglyme, at temperatures between about −10° C. and about +10° C., in the presence of a molar equivalent of an inorganic base selected from the group consisting of NaOH, $Na_2CO_3$, $K_2CO_3$, $NaHCO_3$, and $KHCO_3$, or an organic base selected from the group consisting of pyridine, quinoline, and triethylamine. Furthermore, it has been found that the compounds of formula (I), wherein $R_1$ may be the radical C or the radical D, can be prepared from the compounds of formula (I) wherein $R_1$ is the radical A or the radical B, respectively, by treatment in an aprotic chlorinated solvent selected from $CH_2Cl_2$, $CHCl_3$, $CCl_4$, tetrachloroethane, and trichloroethylene, with an excess of a Lewis' acid selected from $BCl_3$, $BBr_3$, $BF_3$, $AlCl_3$, and $FeCl_3$, or with a hydrogen halide acid selected from HCl and HBr, dissolved in a $C_1$-$C_4$ alcoholic solvent, at temperatures between about −30° C. and about +10° C.

It has been found also that the compounds of formula (I) are endowed with a remarkable antibacteric activity against gram-positive and gram-negative pathogenous bacteria such as, for instance, *Staphylococcus albus, Bacillus pumilus, Proteus morgani*, and *Escherichia coli* ATCC 8739. As example, the M.I.C. (minimum inhibitory concentration) of compound 3, determined according to the method described by Marimount-Wentz in Am. J. Clin. Path. 45, 548, (1960) and by Mac Lowry et al. in Appl. Microbiol. 20, 46, (1970) against S. albus is 0.48 mcg/ml; B. pumilus 1.95 mcg/ml; P. morgani 15.6 mcg/ml; and E. coli 15.6 mcg/ml. Ampicilline shows an M.I.C. against the same bacteria equal to 3.9 mcg/ml; 1.95 mcg/ml, 15.6 mcg/ml and 31.2 mcg/ml, respectively. Therefore, it is possible to use the compounds of formula (I) or a salt thereof acceptable from the physiological point of view in dosages between about 1 and about 100 mg/kg/day by oral or parenteral route administered in a single dose or by dividing the daily dosage into two or four administrations.

The pharmaceutical compositions of the present invention contain the compounds of formula (I) and, optionally, an inert carrier acceptable from the physiological point of view. The preparation can be made up, for example, as capsules, tablets, or syrups suitable for oral administration, or as sterile aqueous solutions, or as a lyophilized powder for parenteral administration. Obviously, the formulations are prepared according to the usual pharmaceutical procedure.

The following examples illustrate the preparation of the compounds according to the present invention, but they are in no way limitative, especially as to the preparation methods.

EXAMPLE 1

There are dissolved 2.017 g ampicilline 0.3H₂O in 100 ml H₂O by the aid of 925 mg NaHCO₃. The solution is cooled to +5° C. and then 1.6 g of 1,2-3,4-diisopropylidene-6-O-chloroformyl-D-galactopyranoside dissolved in 20 ml acetone is added thereto.

The whole solution is stirred for 2 hours at +5° C., thereafter is extracted with ether (3×50 ml), and finally acidified with diluted HCl, at 0° C., up to pH 2.

A further extraction is then carried out with CH₂Cl₂ (3×50 ml) followed by washing with water, drying on Na₂SO₄ and evaporation under vacuum to dryness. The obtained amorphous solid is crystallized from ethyl acetate/petroleum ether (1:1). There is obtained 1.5 g of 6-[D(−)-α-(1,2-3,4-diisopropylidene-D-galactopyranoside-6-O-carboxamido)-phenylacetamido]-3,3-dimethyl-7-oxo-4-thia-1-azabicyclo-[3,2,0]-heptane-2-carboxylic acid (compound 1).

m.p.=158°–160° C.

Analysis for $C_{29}H_{37}N_3O_{11}S$:

|                | C     | H    | N    |
|----------------|-------|------|------|
| calculated (%) | 54.79 | 5.87 | 6.61 |
| found (%)      | 54.76 | 5.94 | 6.32 |

U.V. (95% EtOH+1 eq. NaOH) 212 mμ (ε 55,500).

$[\alpha]_D^{20} = +57.6°$ (c=1 in 95% EtOH+1 eq. NaOH).

By working as described above, the hereinbelow specified compounds are prepared:

Compound 2

7-[D(−)-α-(1,2-3,4-diisopropylidene-D-galactopyranoside-6-O-carboxamido)-phenylacetamido]-3-methyl-8-oxo-5-thia-1-azabicyclo-[4,2,0]-oct-2-ene-2-carboxylic acid;

m.p.=158°–165° C. (ethyl acetate).

Analysis for $C_{29}H_{35}N_3O_{11}S$:

|                | C     | H    | N    |
|----------------|-------|------|------|
| calculated (%) | 54.97 | 5.57 | 6.63 |
| found (%)      | 54.02 | 5.46 | 6.20 |

U.V. (95% EtOH+1 eq. NaOH) 258 mμ (ε12,000) 212 mμ (ε58,000).

$[\alpha]_D^{20} = +17.4°$ (c=1 in 95% EtOH+1 eq. NaOH).

Compound 3

6-[D](−)-α-(1,2-5,6-diisopropylidene-D-glucofuranoside-3-O-carboxamido)-phenylacetamido]-3,3-dimethyl-7-oxo-4-thia-1-azabicyclo-[3,2,0]-heptane-2-carboxylic acid; amorphous;

m.p.=130°–150° C.

Analysis for $C_{29}H_{37}N_3O_{11}S$:

|                | C     | H    | N    |
|----------------|-------|------|------|
| calculated (%) | 54.79 | 5.87 | 6.61 |

| | C | H | N |
|---|---|---|---|
| found (%) | 55.40 | 5.94 | 6.32 |

U.V. (95% EtOH + 1 eq. NaOH) 211 mμ (ε55,000).
$[\alpha]_D^{20} = +49°$ (c = 1 in 95% EtOH + 1 eq. NaOH).

Compound 4

7-[D(−)-α-(1,2-5,6-diisopropylidene-D-glucofuranoside-3-O-carboxamido)-phenylacetamido]-3-methyl-8-oxo-5-thia-1-azabicyclo-[4,2,0]-oct-2-ene-2-carboxylic acid; amorphous;
m.p. = 150°–160° C.;
Analysis for $C_{29}H_{35}N_3O_{11}S$:

| | C | H | N |
|---|---|---|---|
| calculated (%) | 54.97 | 5.57 | 6.63 |
| found (%) | 55.11 | 5.57 | 6.48 |

U.V. (95% EtOH + 1 eq. NaOH) 257 mμ (ε12,700) 212 mμ (ε66,500);
$[\alpha]_D^{20} = +29.5°$ (c = 1 in 95% EtOH + 1 eq. NaOH).

EXAMPLE 2

A solution of 3 g of compound 2 in 60 ml chloroform is cooled to −5° C. and treated with 2.5 ml of anhydrous hydrochloric acid dissolved in ethyl alcohol (21.4% w/v). The mixture is left to stand for 48 hours at +4° C. and thereafter the liquid is decanted from the precipitated tacky product. The product is washed twice by decantation with chloroform and then is solified by rubbing in the presence of isopropyl ether. The formed solid is filtered off, washed with isopropyl ether, and dried under vacuum.

There is obtained 1.9 g of 7-[D(−)-α-(D-galactose-6-O-carboxamido)-phenylacetamido]-3-methyl-8-oxo-5-thia-1-azabicyclo-[4,2,0]-oct-2-ene-2-carboxylic acid (compound 5).
m.p. = 140° C. (decomposition);
Analysis for $C_{23}H_{29}N_3O_{12}S$:

| | C | H | N |
|---|---|---|---|
| calculated (%) | 48.28 | 5.07 | 7.34 |
| found (%) | 48.36 | 5.15 | 7.11 |

U.V. (95% EtOH + 1 eq. NaOH) 304 mμ (ε4,200).
By working as described above, the hereinbelow compounds are prepared:

Compound 6

6-[D(−)-α-(D-galactose-6-O-carboxamido)-phenylacetamido]-3,3-dimethyl-7-oxo-4-thia-1-azabicyclo-[3,2,0]-heptane-2-carboxylic acid.
m.p. = 150° C. (decomposition);
Analysis for $C_{23}H_{31}N_3O_{12}S$:

| | C | H | N |
|---|---|---|---|
| calculated (%) | 48.11 | 5.40 | 7.32 |
| found (%) | 47.15 | 5.42 | 6.95 |

Compound 7

7-[D(−)-60 -(D-glucose-3-O-carboxamido)-phenylacetamido]-3-methyl-2-oxo-5-thia-1-azabicyclo-[4,2,0]-oct-2-ene-2-carboxylic acid.
m.p. = 150° C. (decomposition);
Analysis for $C_{23}H_{29}N_3O_{12}S$:

| | C | H | N |
|---|---|---|---|
| calculated (%) | 48.28 | 5.42 | 7.34 |
| found (%) | 48.40 | 6.95 | 7.40. |

U.V. (95% EtOH + 1 eq. NaOH) 304 mμ (ε3,600).

Compound 8

6-[D(−)-α-(D-glucose-3-O-carboxamido)-phenylacetamido]-3,3-dimethyl-7-oxo-4-thia-1-azabicyclo-[3,2,0]-heptane-2-carboxylic acid;
m.p. = 135° C. (decomposition);
Analysis for $C_{23}H_{31}N_3O_{12}S$:

| | C | H | N |
|---|---|---|---|
| calculated (%) | 48.11 | 5.40 | 7.32 |
| found (%) | 47.57 | 5.78 | 7.15. |

What is claimed is:
1. A penicillanic and cephalosporanic derivative of the formula (I):

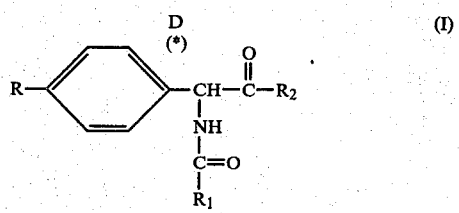

wherein R is H or —OH; $R_1$ is a hexose carbohydrate radical selected from the group consisting of 3-O-glucose, 6-O-galactose, 3-O-glucose acetals, 3-O-glucose ketals, 6-O-galactose acetals, and 6-O-galactose ketals, $R_2$ is a member selected from the group consisting of

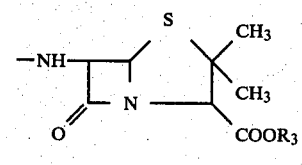

and

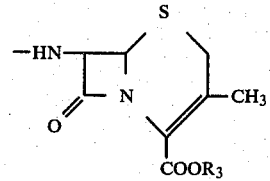

and $R_3$ is H or an alkali or earth-alkaline metal.
2. The penicillanic and cephalosporanic derivative of claim 1, characterized in that the derivatives of the hexose are prepared by reacting it with suitable reagent selected from the group consisting of benzaldehyde, acetone, and cyclohexanone.

3. 6-[D(—)-α-(1,2-3,4-diisopropylidene-D-galactopyranoside-6-O-carboxamido)-phenylacetamido]-3,3-dimethyl-7-oxo-4-thia-1-azabicyclo-[3,2,0]-heptane-2-carboxylic acid.

4. 7-[D(—)-α-(1,2,-3,4-diisopropylidene-D-galactopyranoside-6-O-carboxamido)-phenylacetamido]-3-methyl-8-oxo-5-thia-1-azabicyclo-[4,2,0]-oct-2-ene-2-carboxylic acid.

5. 6-[D(—)-α-(1,2-5,6-diisopropylidene-D-glucofuranoside-3-O-carboxamido)-phenylacetamido]-3,3-dimethyl-7-oxo-4-thia-1-azabicyclo-[3,2,0]-heptane-2-carboxylic acid.

6. 7-[D(—)-α-(1,2-5,6-diisopropylidene-D-glucofuranoside-3-O-carboxamido)-phenylacetamido]-3-methyl-8-oxo-5-thia-1-azabicyclo-[4,2,0]-oct-2-ene-2-carboxylic acid.

7. 7-[D(—)-α-(D-galactose-6-O-carboxamido)-phenylacetamido]-3-methyl-8-oxo-5-thia-1-azabicyclo-[4,2,0]-oct-2-ene-2-carboxylic acid.

8. 6-[D(—)-α-(D-galactose-6-O-carboxamido)-phenylacetamido]-3,3-dimethyl-7-oxo-4-thia-1-azabicyclo-[3,2,0]-heptane-2-carboxylic acid.

9. 7-[D(—)-α-(D-glucose-3-O-carboxamido)-phenylacetamido]-3-methyl-2-oxo-5-thia-1-azabicyclo-[4,2,0]-oct-2-ene-2-carboxylic acid.

10. 6-]D(—)-α-(D-glucose-3-O-carboxamide)-phenylacetamido]-3,3-dimethyl-7-oxo-4-thia-1-azabicyclo-[3,2,0]-heptane-2-carboxylic acid.

11. 6-[D(—)-α-(1,2-3,4-diisopropylidene-D-galactopyranoside-6-O-carboxamido)-p-hydroxyphenylacetamido]-3,3-dimethyl-7-oxo-4-thia-1-azabicyclo-[3,2,0]-heptane-2-carboxylic acid.

12. 4-[D(—)-α-(1,2-5,6-diisopropylidene-D-glucofuranoside-3-O-carboxamido)-p-hydroxyphenylacetamido]-3,3-dimethyl-7-oxo-4-thia-1-azabicyclo-[3,2,0]-heptane-2-carboxylic acid.

13. 6-[D(—)-α-(D-galactose-6-O-carboxamido)-p-hydroxyphenylacetamido]-3,3-dimethyl-7-oxo-4-thia-1-azabicyclo-[3,2,0]-heptane-2-carboxylic acid.

14. 6-[D(—)-α-(D-glucose-3-O-carboxamido)-p-hydroxyphenylacetamido]-3,3-dimethyl-7-oxo-4-thia-1-azabicyclo-[3,2,0]-heptane-2-carboxylic acid.

15. A process for the preparation of a penicillanic and cephalosporanic derivative of the formula:

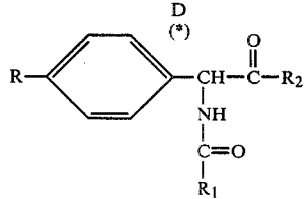

wherein
R is H or —OH;
R₁ is a hexose carbohydrate radical selected from the group consisting of 3-O-glucose, 6-O-galactose, 3-O-glucose acetals, 3-O-glucose ketals, 6-O-galactose acetals, and 6-O-galactose ketals,
R₂ is a member selected from the group consisting of:

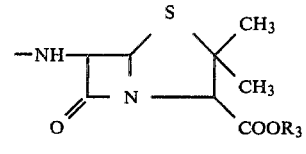

and

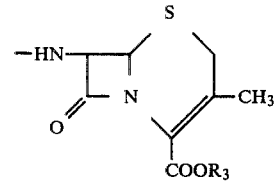

wherein R₃ is H or an alkali or alkaline earth metal comprising reacting a compound of the formula:

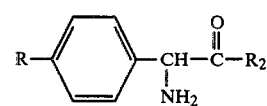

where R and R₂ are as previously defined with a compound of the formula:

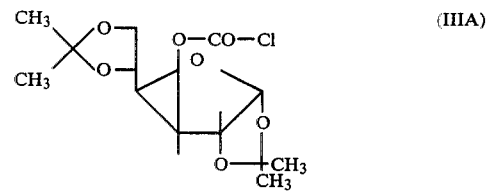

or

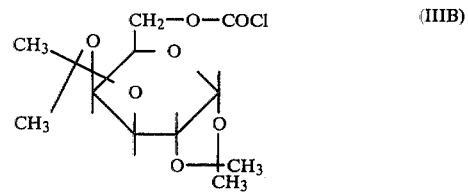

in an aqueous medium in the presence of water-miscible organic solvent at a temperature of from about −10° C. to about +10° C. in the presence of a base.

16. The process of claim 15, wherein said water-miscible organic solvent is selected from the group consisting of acetone, tetrahydrofurane, dioxane, and diglyme.

17. The process of claim 15, wherein said base is an inorganic base selected from the group consisting of NaOH, Na₂CO₃, K₂CO₃, NaHCO₃, and KHCO₃.

18. The process of claim 15, wherein said base is an organic base selected from the group consisting of pyridine, quinoline, and triethylamine.

19. The process of any one of claims 15, 16, 17, and 18, wherein said base is present in an amount corresponding to a molar equivalent.

20. The process of claim 15, wherein the reaction product is treated in a chlorinated aprotic solvent with an excess of a reagent selected from Lewis' acids and hydrogen halide acids, the acid is dissolved in a C₁-C₄ alcoholic solvent, and the reaction is carried out at a temperature between about −30° C. and about +10° C.

21. The process of claim 20, wherein said chlorinated aprotic solvent is selected from the group consisting of $CH_2Cl_2$, $CHCl_3$, $CCl_4$, ethanetetrachloride, and trichloroethylene.

22. The process of claim 20, wherein said Lewis' acid is selected from the group consisting of $BCl_3$, $BBr_3$, $BF_3$, $AlCl_3$, and $FeCl_3$.

23. The process of claim 20, wherein said hydrogen halide acid is selected from the group consisting of HCl and HBr.

24. The process of claim 20, wherein an excess of Lewis' acid or the hydrogen halide acid is used.

25. An antibacterial pharmaceutical composition comprising:
   an antibacterially effective amount of a compound of the formula:

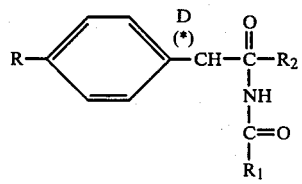

wherein R is H or —OH;

$R_1$ is a hexose carbohydrate radical selected from the group consisting of 3-O-glucosoe, 6-O-galactose, 3-O-glucose acetals, 3-O-glucose ketals, 6-O-glactose acetals, and 6-O-galactose ketals, $R_2$ is a member selected from the group consisting of

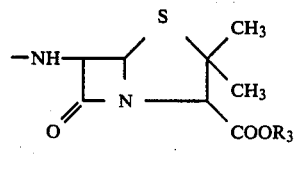

and

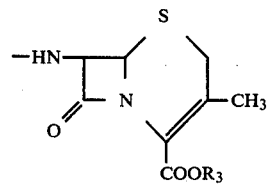

and wherein $R_3$ is H or an alkali or alkaline earth metal and a pharmaceutically acceptable excipient or vehicle.

26. The pharmaceutical composition of claim 25, wherein the compound of formula (I) is present in a pharmaceutically acceptable salt form.

27. The pharmaceutical composition of claim 25, wherein the compound of formula (I) is present in an amount of between about 1 and about 100 mg/kg.

28. The pharmaceutical composition of claims 25, 26, or 27, in capsule, tablet, or syrup form for oral administration and containing an inert pharmacologically acceptable carrier.

29. The pharmaceutical composition of claim 25, in a sterile aqueous solution or lyophylized powder form for parenteral administration.

* * * * *